(12) United States Patent
Filho et al.

(10) Patent No.: US 6,896,694 B1
(45) Date of Patent: May 24, 2005

(54) DEVICE FOR DISOBSTRUCTION OF ATERIOSCLEROTIC LESIONS WHICH INCORPORATE THE ORIGIN OF LATERAL BRANCHES, OR WHICH ARE LOCATED IN BIFURCATION OF THE CORONARY CIRCULATION, AND RESPECTIVE INTERVENTIONIST PROCESS OF PLACING SUCH DEVICE

(75) Inventors: Eulógio Emilio Martinez Filho, São Paulo (BR); Marco Antonio Perin, São Paulo (BR)

(73) Assignee: Fundaco Zerbini A Brazilian Foundation, Sao Paulo Cep (BR)

( * ) Notice: Subject to any disclaimer, the term of this patent is extended or adjusted under 35 U.S.C. 154(b) by 0 days.

(21) Appl. No.: 09/573,454

(22) Filed: May 17, 2000

(30) Foreign Application Priority Data

May 17, 1999 (BR) .......................................... 9901540-4

(51) Int. Cl.[7] .................................................. A61F 2/06
(52) U.S. Cl. ..................................... 623/1.11; 623/1.15
(58) Field of Search ............................... 623/1.11–1.23, 623/1.35

(56) References Cited

U.S. PATENT DOCUMENTS

| | | |
|---|---|---|
| 5,263,932 A | 11/1993 | Jang |
| 5,308,356 A | 5/1994 | Blackshear, Jr. et al. |
| 5,338,300 A | 8/1994 | Cox |
| 5,366,504 A * | 11/1994 | Andersen et al. ............ 623/1.5 |
| 5,383,856 A | 1/1995 | Bersin |
| 5,607,445 A | 3/1997 | Summers |
| 5,662,675 A | 9/1997 | Polanskyj Stockert et al. |
| 5,713,917 A | 2/1998 | Leonhardt et al. |
| 5,746,766 A | 5/1998 | Edoga |
| 5,755,735 A | 5/1998 | Richter et al. |
| 5,868,777 A | 2/1999 | Lam |
| 6,096,073 A * | 8/2000 | Webster et al. ............ 623/1.16 |
| 6,325,826 B1 * | 12/2001 | Vardi et al. ................ 623/1.35 |

FOREIGN PATENT DOCUMENTS

FR 2722678 1/1996

* cited by examiner

*Primary Examiner*—Corrine McDermott
*Assistant Examiner*—Thomas Barrett
(74) *Attorney, Agent, or Firm*—Katten Muchin Zavis Rosenman

(57) ABSTRACT

A device, for disobstructing ateriosclerotic lesions in proximity to the origin of lateral branches or bifurcations of an artery. The device includes a stent having two sections. One section is adhered along approximately two thirds of its total length to a balloon. The other section corresponds to the final third of the length of the stent does not completely adhere to the balloon and is partially expanded before its use. A proximal end of a metallic guide wire passes through the mesh of the partially expanded section which has been previously introduced into a secondary branch or bifurcation in the artery. The wire provides an access to the secondary branch for introducing a second balloon or a second stent for the disobstruction of the secondary branch or bifurcation.

7 Claims, 3 Drawing Sheets

DEVICE FOR DISOBSTRUCTION OF ATERIOSCLEROTIC LESIONS WHICH INCORPORATE THE ORIGIN OF LATERAL BRANCHES, OR WHICH ARE LOCATED IN BIFURCATION OF THE CORONARY CIRCULATION, AND RESPECTIVE INTERVENTIONIST PROCESS OF PLACING SUCH DEVICE

BACKGROUND AND SUMMARY OF THE INVENTION

Diagnostic catheters are employed for the diagnosis of patients with coronary insufficiency, more specifically, with ateriosclerosis (arteriosclerosis caused by atheromas). The diagnostic catheters typically consist of specially configured tubes to allow their introduction into the coronary arteries and to enable the injection of a contrast fluid for x-rays of the coronary arteries. While contrast fluid is injected, radiographic pictures are taken to detect the possible obstruction points of the arteries, which result from the atheroma process.

If an obstruction is verified, this may lead to a medical procedure called a coronary transluminal angioplasty, which involves removing the obstruction from the blocked artery to improve blood flow. According to this procedure, a special tube is first placed in the patient, which is called a guide catheter, and, through the guide catheter, a fine wire is introduced, called the guide wire, which moves through the obstructed part of the compromised artery to be treated. Then, taking advantage of the guide wire, a second or balloon catheter slides over the guide wire. The end of the balloon catheter is equipped with a balloon, which is positioned along the entire obstructed section of the artery. The balloon is then inflated, one or more times, pressing the atheromas against the wall of the blood vessel or artery. Thus, the diameter of the vessel is increased, and the flow of blood is improved. Once the artery is disobstructed, the balloon catheter and the guide wire are removed. A radiographic image using contrast is then obtained of the disobstructed artery observe the result. Finally, the guide catheter is removed, completing the coronary angioplasty.

Unfortunately, it is not uncommon after the balloon angioplasty to observe a new reduction of the caliber of the blood vessel that has been treated. More so recently, in order to reduce the risk of a new obstruction forming, the coronary angioplasty has been accompanied by an additional procedure, the implantation of a device called the coronary stent.

A stent device is configured using a metallic tube, the wall of which is formed by a mesh of flexible metallic wires which are conveniently doubled and interconnected among themselves. In an initial position, the mesh, or rather, the folds of its wires, are absolutely closed, so as to form a tube with a rather reduced diameter. The mesh of metallic wires, which forms the wall of the stent, is capable of being unfolded, so as to bring about the radial expansion of the tube. This radial expansion is provoked by the inflation or insufflation of a balloon that is previously adhered to the stent along its entire length.

Thus, during the coronary angioplasty procedure described above, as soon as the disobstruction of the artery has been concluded, another balloon catheter equipped with the coronary stent discussed above is introduced into the artery. Once the stent is positioned along the recently disobstructed section or stretch, the balloon is inflated, which causes the radial expansion of the stent. The wall of the stent, with the metallic wires now expanded, further presses the atheroma plaque against the wall of the blood vessel, which has already been pressed by the first or previous balloon catheter. Once expanded, the stent is released from the balloon, and adheres to the vessel, and the balloon catheter which expanded the stent is removed, leaving only the stent.

The devices and the techniques normally used in the procedure to disobstruct compromised arteries (with ateriosclerotic lesions) have proven to be relatively efficient in a large number of the cases. However, when the ateriosclerotic lesions agglomerate at the origin of lateral arterial branches, or when they are localized in arterial bifurcations of the coronary circulation system, the implantation of stents frequently raises concerns. Until now these concerns have yet to be solved, whether for the obstruction of a lateral branch or for lesions formed in arterial bifurcations. These concerns result from the compression of the atheroma plaque against the wall of the blood vessel upon expansion of the stent. This may cause the reduction in the caliber of the opening that provides access to the secondary branch (ostium of the branch), and often results in total obstruction. In this case, the stent becomes a potential impediment to the passage of any disobstruction element or device for the ostium.

This invention is directed to a device having a conventional balloon catheter, the balloon of which supports a stent arranged in accordance with the principles of the present invention. The stent does not totally adhere to the balloon along the length of the stent. The stent has two sections. One section, which is preferably approximately two thirds of the total length of the stent, is firmly adhered to the balloon, as provided for in conventional stents. The other section, preferably corresponding to the other third of the length of the stent, does not adhere to the balloon and is partially expanded before its use, so as to enable passage through the mesh of an appropriate metallic guide wire. This metallic wire is previously introduced into a secondary branch or bifurcation in proximity to the obstruction. In the case of lesions located in proximity to arterial bifurcations, the guide wire leads to one of the branches, and will serve to guide the second balloon to the ostium of the branch. The metallic wire enables a second stent or a second angioplasty balloon to be introduced after disobstructing the main artery through the traditional method of coronary angioplasty and stent placement, if the second branch or bifurcation becomes blocked.

During the disobstruction of the main artery by the traditional method of coronary angioplasty and stent implantation, the secondary artery may become blocked. In other words, the subject invention maintains through the mesh of the new device a stationary wire in the secondary branch. This wire may be used as an access to the secondary branch if necessary and enables introduction of an element having a second balloon or stent for the disobstruction of the ostium.

This invention is also directed to a new method for implanting a stent. Although it includes some procedures already employed in the traditional method of coronary angioplasty followed by the implanting of the stent, the subject invention presents a sequence of new procedures and interferences, capable of permitting the adequate use of the new device.

BRIEF DESCRIPTION OF THE SEVERAL VIEWS OF THE DRAWINGS

The drawings, which form an integral part of the specification, are to be read in conjunction therewith, and like reference numerals are employed to designate identical components in the various views:

FIG. 2 illustrates the arterial segment with ramification (bifurcation) of coronary circulation caused by the obstructive ateriosclerotic process to be treated, through which passes a guide catheter (not illustrated), two guide wires, one of which moves over the arterial lesion, and the other which reaches the secondary branch;

FIG. 3 illustrates the passage of the stent from the proximal extremity of the guide wire previously placed in the artery through the span of the balloon catheter, and the passage of the proximal extremity of the other guide wire previously placed in the secondary branch through the mesh of a stretch or segment that does not adhere to the artery and is partially expanded;

FIG. 4 illustrates the device following compression of the stretch or segment of the stent previously expanded by the balloon, the device being in the configuration which will be inserted into the primary or main compromised artery and will be positioned along the stretch to be disobstructed, which is shown in FIG. 5;

FIG. 6 illustrates the device after inflating the balloon, which caused the expansion and the consequent adherence of the stent to the internal wall of the vessel; and FIG. 7 illustrates the guide wire previously placed in the lateral branch which enables the placement of another balloon catheter, which also passes through the stent, and reaches the ostium of the secondary branch, where the second balloon is inflated to disobstruct the ostium.

DETAILED DESCRIPTION OF THE INVENTION

Figure 1:
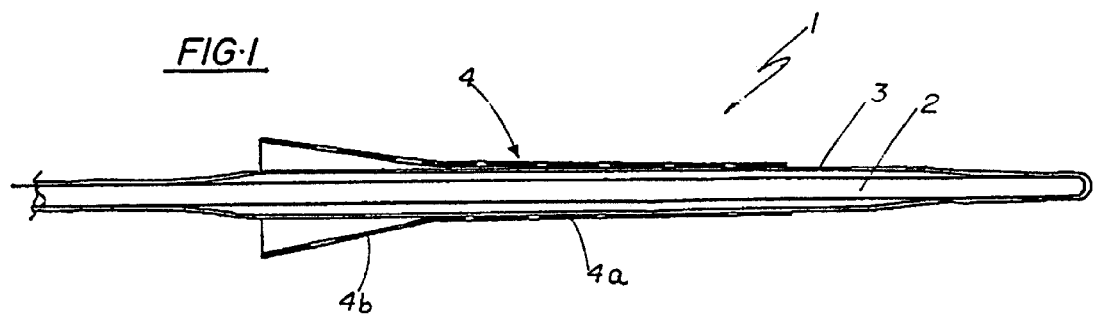
FIG. 1 is a lateral, cross-sectional view of the device in accordance with the principles of the present invention.

The purpose of this invention is to provide a device for disobstruction of aterlosclerotic lesions which incorporates the origin of lateral branches or which are located in the bifurcation of the coronary circulation system and the respective procedure of placing such device. With reference to FIG. 1, the device 1 includes a balloon catheter 2 which is of a conventional type. The balloon 3 3 is covered by a stent 4. Stent 4 is embodied as a metallic tube, the wall of which is formed by a flexible metallic wire mesh formed of wires conveniently doubled and interconnected among themselves. The wires may be unfolded by the inflation or insulation of the balloon 3 of the balloon catheter 2.

The device 1 includes several features. First, the stent 4 does not adhere to the balloon 3 of the balloon catheter 2 along its entire length. Rather, the stent 4 has two sections or stretches. One section 4a firmly adheres to the balloon 3 (preferably with approximately two thirds of its total length), and the other section 4b (preferably corresponding to the other third of its total length) does not adhere to the balloon 3 and further partially expands, prior to its use. This enables passage through its mesh of an appropriate metallic wire 5 previously introduced in the secondary branch R of the artery A, which is shown having the obstructive arteriosclerotic process to be treated. Alternatively, the subject device may be used in arteries having lesions to be treated located in one of the branches of an arterial bifurcation. The wire 5 is inserted in a second or secondary branch R, and may be used as a means of access to the second or secondary branch if necessary, should the ostium O suffer from a reduction or total obstruction of its caliber. In such a case, wire 5 provides an element that bears a second balloon or possibly a second stent for the disobstruction of the ostium.

Figure 8A:
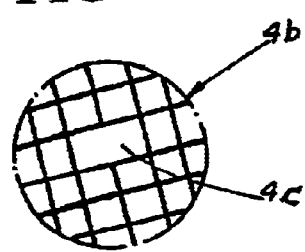
FIGS. 8A and 8B are details the detail A indicated in FIG. 3 illustrating two possible examples of the stent mesh, which upon partial expansion of the stent, provides a larger opening than those of the other openings, for the passage of the guide wire previously placed in the secondary branch, so as to facilitate the later passage, through said mesh, of the second balloon catheter, or even a second stent, if necessary.
Figure 8B:
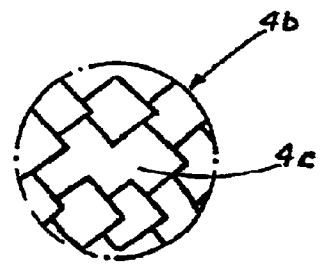

Optionally, in the stretch 4b of the stent 4 the wire presents an opening 4c, as shown in FIG. 8, of greater dimensions than those of the other openings, for the passage of the guide wire previously placed in the secondary branch R, to facilitate the later passage through the mesh of the second balloon catheter or a second stent.

The process for placing the device 1 will be described as follows in conjunction with FIGS. 2 to 7.

Initially, an angioplasty guide catheter (not shown) is inserted into the patient. The ostium O of the coronary artery which has the obstructive ateriosclerotic process to be treated is selectively characterized. Through the guide catheter, a metallic wire 5 (guide wire or conduction wire) is inserted into the main or primary artery A. The metallic wire 5 is introduced into the second or secondary branch R that originates in the compromised arterial section, shown in FIG. 2. In cases of lesions located in arterial bifurcations, the wire 5 is positioned in one of the branches involved and defined as a second or secondary branch.

Figure 2:
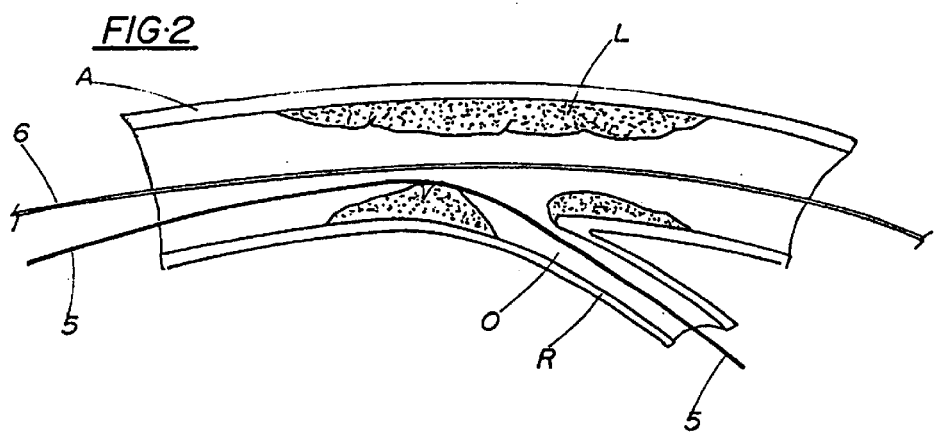
FIGS. 2 to 7 illustrate, in sequence, various cross-sectional views for utilizing the subject invention, in particular.
Figure 3:
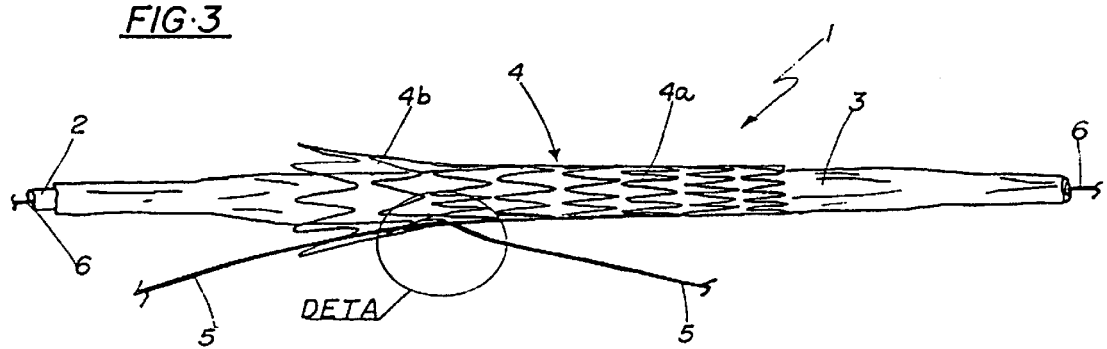
Figure 4:
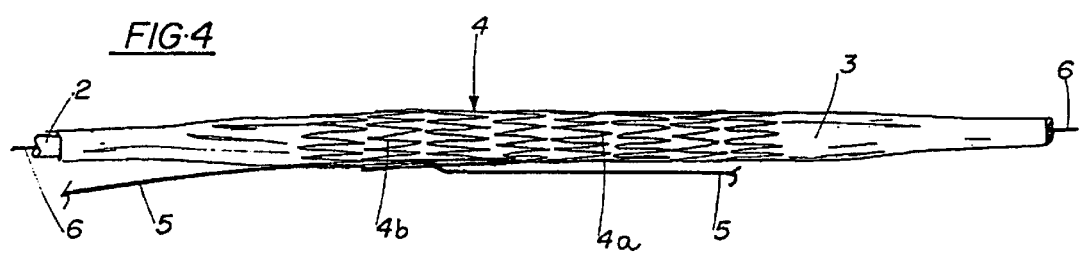

A second metallic wire 6 (also a guide wire or conduction wire) is introduced into the artery A through the guide catheter, until it moves over the obstructive lesion L to be treated, shown in FIG. 2.

Through the inflation or insufflation of a first angioplasty balloon guided to the lesion L through a guide wire 6, a pre-dilation of the blood vessel or artery is obtained. If there is an obstructive lesion in the ostium O of the secondary branch R, or of one of the branches of a bifurcation, a second balloon is guided to the second or secondary branch through the corresponding guide wire 5. The second balloon is pre-dilated as well. The balloons used for the pre-dilations are then withdrawn, while the wires 5 and 6 are maintained in position in the respective distal beds of the secondary branch R and of the main artery A.

The device 1 of the subject invention is then prepared. For that purpose, it is passed through the proximal end or extremity of the guide wire 5 which was previously placed in the second or secondary branch R or in one of the branches of the bifurcation. The guide wire 5 is routed through the stent mesh 4 and, more specifically, through the mesh section 4b. The device 1 is also passed through the proximal end or extremity of the guide wire 6 which was previously placed in the main or primary artery A through the balloon catheter 2 of the device 1 (see FIG. 3). Section 4b is then pressed on the balloon 3, so that the entire extension of the stent 4 firmly adheres to balloon 3. The wire 5 is positioned between the stent 4 and the balloon 3, shown in FIG. 4. Device 1 in this configuration will be positioned in the main or primary compromised artery A, and will be positioned along the stretch with the lesion L to be disobstructed.

Figure 5:
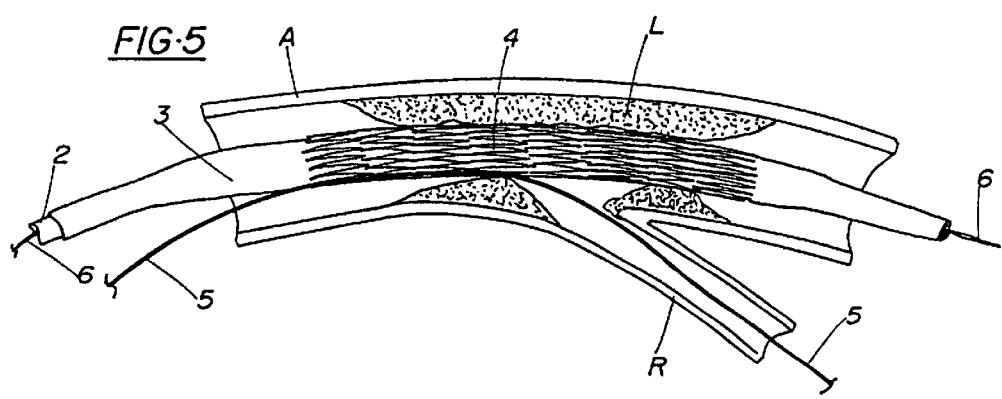
Figure 6:
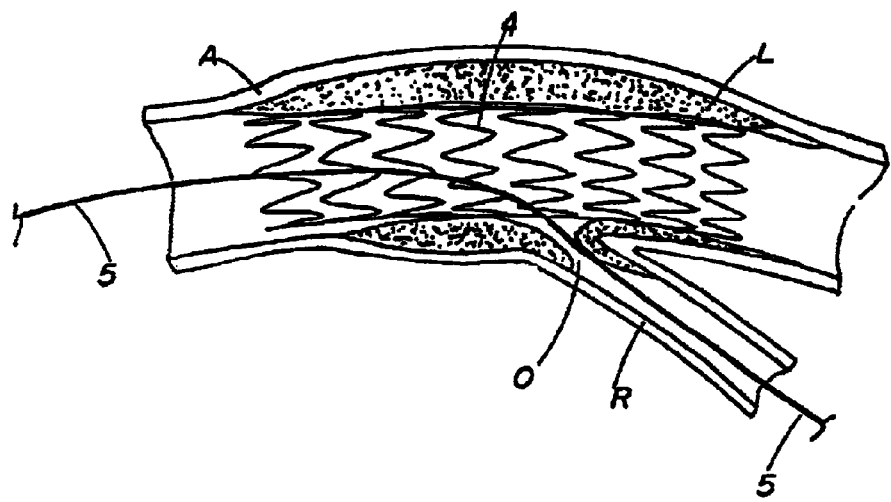

Thus, with the proximal end or extremity of the guide wire 6 having already been placed through the span of the balloon catheter 2, the balloon 3 is inserted into the artery A up to the section of the obstructive lesion L, (shown in FIG. 5). The guide wire 5 has already been placed through the mesh of the stent 4 and is maintained between the stent 4 and the balloon 3 while the device is inserted into the artery.

Once the balloon 3 is properly positioned with respect to the lesion L, the inflation of the balloon 3 is carried out, which causes the expansion of the stent 4 and its consequent release from the balloon 3. After the release, the balloon 3 is withdrawn, and the artery A is analyzed using injection of a contrast fluid (see FIG. 6).

Figure 7:
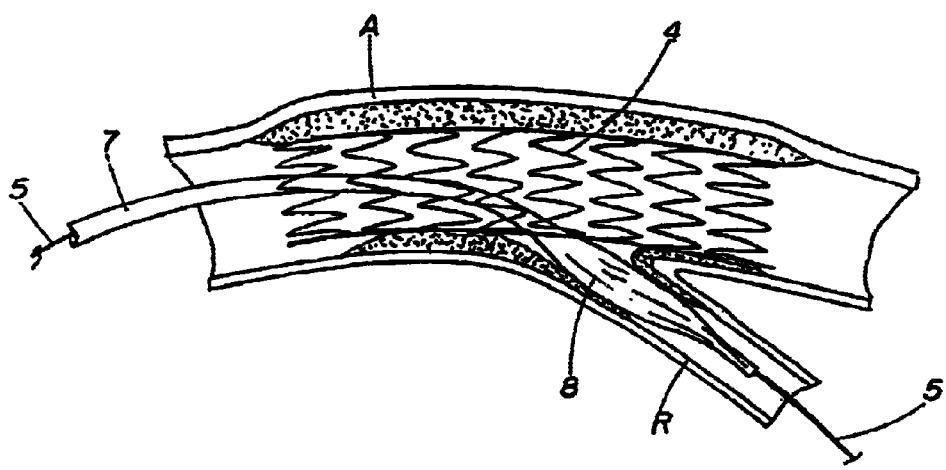

If, as a consequence of the release of the stent 4, there is a reduction in the caliber of the ostium O of the second or secondary branch R, or of one of the branches involved, in the case of lesions in the bifurcations, the guide wire 5 positioned in this branch will be used to introduce another balloon catheter, having a low profile balloon 8 or even with another stent. Either selected device will reach the branch R equally through the stent mesh 4. The balloon 8 is then inflated, which causes the dilation of the branch R, as shown in FIG. 7 to cause disobstruction of branch R. Once the balloon 8 is deflated, the balloon catheter 7 is removed from the artery A, finalizing the angioplasty process with total success.

Certain cases may occur where it may be necessary to use a second higher profile balloon catheter, or even a second stent, to minimize risk of the said balloon catheter and stent not being able to pass over the mesh of the nonadhered and partially expanded section 4b of the stent 4. An optional opening 4c of FIG. 8 may be utilized for this procedure. Opening 4c is of greater dimensions than those of the other openings provided for the passage of the guide wire 5 previously placed in the secondary branch R. Opening 4c assures the free passage of the second balloon catheter 8, or second stent, through the mesh, even if they have a greater profile.

What is claimed is:

1. A device for disobstruction of arteries having obstructions in proximity to primary and secondary branches or bifurcations of the artery, comprising:
    a balloon catheter having a balloon; and
    a stent covering the balloon, the stent having a wall formed by a flexible metallic wire mesh which is constricted prior to inflation of the balloon and expanded upon inflation of the balloon, the stent having two ends, one end adhered to the balloon when the balloon is not inflated, and the other end circumferentially non-attached to and radially spaced from the balloon when the balloon is not inflated, the other end configured to be selectively, partially expanded when the balloon is not inflated to enable passage of a proximal end of a metallic wire previously introduced into the secondary branch of the artery, the wire providing access to the secondary branch, and adapted for guiding one of a second balloon and a second stent unto the secondary branch.

2. The device in accordance with claim 1, wherein the first end of the stent has a length which is approximately two thirds of the total length of the stent, and the other end has a length which is approximately one third of the total length of the stent.

3. The device in accordance with claim 1, wherein the wire mesh of the other end has an opening which is larger than the other openings of the wire mesh of the other end to enable passage of a guide wire placed in the secondary branch.

4. A method of placing a device for disobstruction of arteries having obstructions in proximity to primary and secondary branches or bifurcations of the artery, comprising the steps of:
    inserting an angioplasty guide catheter into the primary branch of artery;
    inserting a first guide wire through the guide catheter and placing the first guide wire in proximity to the obstruction;
    inserting a second guide wire through the guide catheter and positioning the guide wire in the secondary branch;
    inserting a first angioplasty balloon in the artery using the first guide wire and positioning the angioplasty balloon in proximity to the obstruction;
    inflating the angioplasty balloon to cause the predilation of the artery;
    withdrawing the balloon while maintaining the first and second wires in position in the respective primary and secondary branches of the artery;
    passing the proximal end of the second guide wire through a mesh portion of a stent, the mesh portion of the stent being detachable through expansion from a supporting balloon of a supporting balloon catheter to enable passage of the second guide wire through an opening in the wire mesh, and passing the proximal end of the first guide wire through the supporting balloon, the stent having a section circumferentially detached from the supporting balloon when not inflated while a remaining section of the stent stays adhered to the same supporting balloon, the second guide wire being positioned between the stent and the supporting balloon;
    inserting the supporting balloon catheter and the attached stent in proximity to the obstruction, the second guide wire being maintained between the stent and the balloon while the device is introduced into the artery;
    inflating the supporting balloon, causing the stent to expand and be released from the supporting balloon; and
    removing the supporting balloon.

5. The method of claim 4 further comprising the step of injecting contrast fluid to determine if the release of the stent caused a reduction in the caliber of the secondary branch.

6. The method of claim 5 further comprising the steps of:

inserting a second balloon catheter having second balloon and an optional second stent through the second guide wire to the secondary branch by passing second balloon catheter through the mesh of the first stent;

inflating the second balloon to correspondingly dilate the second branch, and thus the obstruction in the secondary branch; and deflating the second balloon and withdrawing the second balloon catheter from the secondary branch and from the artery.

7. A device for disobstruction of arteries having obstructions in proximity to primary and secondary branches or bifurcations of the artery, comprising:

a balloon catheter having a balloon; and a stent covering the balloon, the stent having a wall formed by a flexible metallic wire mesh which is constricted prior to inflation of the balloon and expanded upon inflation of the balloon, the stent having two sections, one section adhered to the balloon when the balloon is not inflated, and the other section circumferentially non-attached to the balloon when the balloon is not inflated, the other section configured to be selectively, partially expanded when the balloon is not inflated to enable passage of a proximal end of a metallic wire previously introduced into the secondary branch of the artery, the wire providing access to the secondary branch, and adapted for guiding one of a second balloon and a second stent into the secondary branch, wherein the wire mesh of the other section has an opening which is larger than the other openings of the wire mesh of the other section to enable passage of a guide wire placed in the secondary branch.

* * * * *